United States Patent [19]

Berger

[11] Patent Number: 5,893,405

[45] Date of Patent: Apr. 13, 1999

[54] TRIANGULAR SPOKE SPRUE

[75] Inventor: Robert P Berger, Encino, Calif.

[73] Assignee: Belle de St. Claire, Chatsworth, Calif.

[21] Appl. No.: 08/957,723

[22] Filed: Oct. 24, 1997

Related U.S. Application Data

[62] Division of application No. 08/601,074, Feb. 12, 1996, Pat. No. 5,688,533.

[51] Int. Cl.⁶ .................................. B22C 7/02; B22C 9/04
[52] U.S. Cl. ........................... 164/244; 164/35; 164/36; 164/45; 249/54; 249/62; 425/175; 425/DIG. 11
[58] Field of Search ........................... 249/61, 62, 175, 249/54; 425/175, 176, DIG. 11; 433/201.1, 202.1, 206; 164/34, 35, 36, 45, 235, 244

[56] References Cited

U.S. PATENT DOCUMENTS

| | | |
|---|---|---|
| 4,081,019 | 3/1978 | Kulig ............................. 164/34 |
| 4,558,841 | 12/1985 | Engelman et al. ............. 249/54 |
| 4,573,921 | 3/1986 | Berger . |
| 4,603,728 | 8/1986 | Rousseau ....................... 164/244 |
| 4,898,359 | 2/1990 | Gopon . |
| 4,972,897 | 11/1990 | Thomas .......................... 164/35 |
| 5,044,419 | 9/1991 | Ware .............................. 164/34 |
| 5,281,122 | 1/1994 | Langer . |
| 5,338,192 | 8/1994 | Weber . |
| 5,406,999 | 4/1995 | Berger et al. . |

*Primary Examiner*—Jan H. Silbaugh
*Assistant Examiner*—Dae Young Lee
*Attorney, Agent, or Firm*—Wood, Herron & Evans, L.L.P.

[57] ABSTRACT

A mold assembly and sprue configuration for dental investment casting includes a ring shaped casing, a base and a cover all made of resilient plastic material and frictionally engaged with each other. The base includes a raised neck having a top surface with a sighting bead for use in mounting wax forms on the sprue, positioned within the casing. The sprue includes a post for engaging a blind bore in a hub of the base. The cover includes a downwardly extending plug which extends into the body of the casing, and a curved lip with recess for facilitating the pouring of investment solution into the mold. The sprue has three spokes and a ring which are all triangular in cross-section to reduce the amount of metal needed in the precision casting to be made with the invention and also to provide a convenient flat upper surface for mounting wax forms to the sprue.

7 Claims, 3 Drawing Sheets

TRIANGULAR SPOKE SPRUE

This application is a division of application Ser. No. 08/601.074 filed on Feb. 12, 1996, now U.S. Pat. No. 5,688,533.

FIELD AND BACKGROUND OF THE INVENTION

The present invention relates, in general, to plastic molds or castings for making investment molds and, more particularly, to a new and useful round ringless mold and spoked sprue for making investment molds for precision casting of dental prostheses.

In the dental field, it is common to use lost wax methods for producing dental castings Lost wax methods utilize investment solution which is at least partly cured in a vessel in order to produce a dental casting.

In many known casting devices, a metal or plastic ring is force fit into a groove in a base to form the mold or vessel for investing the investment solution.

The use of polyvinyl chloride (PVC) or other elastomer, in the construction of both the base and ring is desirable, among other reasons, because such materials can accommodate expansion of the investment casting as it cures and such materials are more readily cleaned after the hardened investment is removed.

Molds and sprues in this field are illustrated in U.S. Pat. Nos. 4,573,921; Des. Pat. No. 329,900; 5,406,999 and 5,469,908.

Various patents in this field disclose various sprue plus mold structures. See for example U.S. Pat. Nos. 1,458,835; 1,939,479; 2,274,186; 3,648,760; 3,939,898 and 4,558,841.

U.S. Pat. No. 4,962,909 discloses a mold for dentistry which includes a lower funnel shaper for shaping the funnel portion of an investment, and an upper blind funnel for displacing a core portion of the investment from within a pattern of dental forms, to reduce distortion in the forms which would have been caused by an expansion of the investment as it cured.

U.S. Pat. No. 5,183,095 discloses a mold for precision casting made of thermoplastic material.

The advantage of using thermoplastic material for a mold in the field of dental casting has been described in *Materials and Materials Science*, No. 3 Report 303, March 1981, "The Equi-Spansion Technique for Castings Without Metal Rings" by Engelmann and Blechner. The advantages of maintaining uniform investment wall thickness around a wax form set by using an oval mold for making a precision casting has been disclosed in *Trends & Techniques in the Contemporary Dental Laboratory*, Volume 8, No. 3, "The Effects of Shape and Size of Investment Heating and Cooling Rates", by Berger and Benson.

A wax sprue for dental casting is also currently being marketed by American Diversified Dental Systems, known as The Spiroloop. This product comprises a central post or hub, meant to be attached to the base of a mold. Three spokes extend outwardly from the hub and are curved helically. A ring connects the outer ends of the spokes and forms a support for wax forms to be attached to the top of the sprue. The spokes and ring all have circular cross-sections. Accordingly, after the lost wax process is completed, the metal casting includes thick cylindrical and helical spoke segments and a thick ring with cylindrical cross-section. This represents the use of a large quantity of metal. The advantages of the spiral wound spokes are said to include a more quick and smooth flow of metal without the creation of restrictions that cause turbulence.

A need remains for an improved mold with sprue that reduces distortion of the wax forms in the investment casting, reduces the amount of wasted investment casting and reduces the amount of excess metal in the sprue pattern of the precision casting.

SUMMARY OF THE INVENTION

The present invention comprises an improved mold and sprue for the production of dental castings using a lost wax method.

The mold of the present invention receives a liquid investment solution which cures to produce an investment castings The invention comprises a round casing having a collar at an inner surface of a lower end of the casing. The casing is frictionally engaged with a base having a round neck which extends upwardly, in an axial direction or at a slight incline for frictionally engaging the collar of the casing. A sprue with spokes and a ring, or more correctly, a sprue former, carries a plurality of wax forms on the ring and is located on the base for producing the metal precision dental casting.

Both the casing and the base are made of a resilient plastic material such as PVC. The neck of the base is in the form of a ring with a conical or planar upper ring shaped surface. A raised circular bead is formed concentrically on the ring shaped surface, between inner and outer axial faces of the neck.

The bead is used as a sighting tool for the lab technician to use for placement of the wax forms on the ring. All wax forms must be placed inside the sighting bead in order to insure sufficient investment material thickness in the investment casting, around the wax forms The base further comprises a conical hub at a center of the base which supports the wax or plastic sprue or sprue former. A ring shaped groove extends between the inside face of the neck, and the hub. A blind cylindrical hole is provided at the top center of the hub for receiving a post at the bottom of the spoked sprue. The post of the sprue is advantageously tapered with a large diameter bottom and a smaller diameter top. This helps firmly fix the post into the hole of the hub. The ring shaped groove around the hub as well as the conical shape of the hub form the funnel portion of the investment casting while reducing the amount of wasted investment material in the funnel area of the investment casting.

A cover, which, like the casing and base, is also made of elastomer such as PVC, is used to cover the open upper end of the casing. The cover includes an upstanding lip and peripheral opening for receiving liquid investment material, similar to the lip and opening disclosed in U.S. Pat. No. 5,469,908. Depending from the center of the cover is a blind funnel or post which creates a void in the investment casting, near the top center of the mold. This reduces the thickness of investment material around the upper portion of the casing, reducing the tendency of the investment to deform the wax forms which are also spaced around the casing. This is because a uniform wall thickness of investment material is created on both inner and outer sides of the wax forms.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which an embodiment of the invention is illustrated.

DESCRIPTION OF THE PREFERRED EMBODIMENT

The present invention pertains to the production of dental molds using investment casting vessels.

Figure 1:
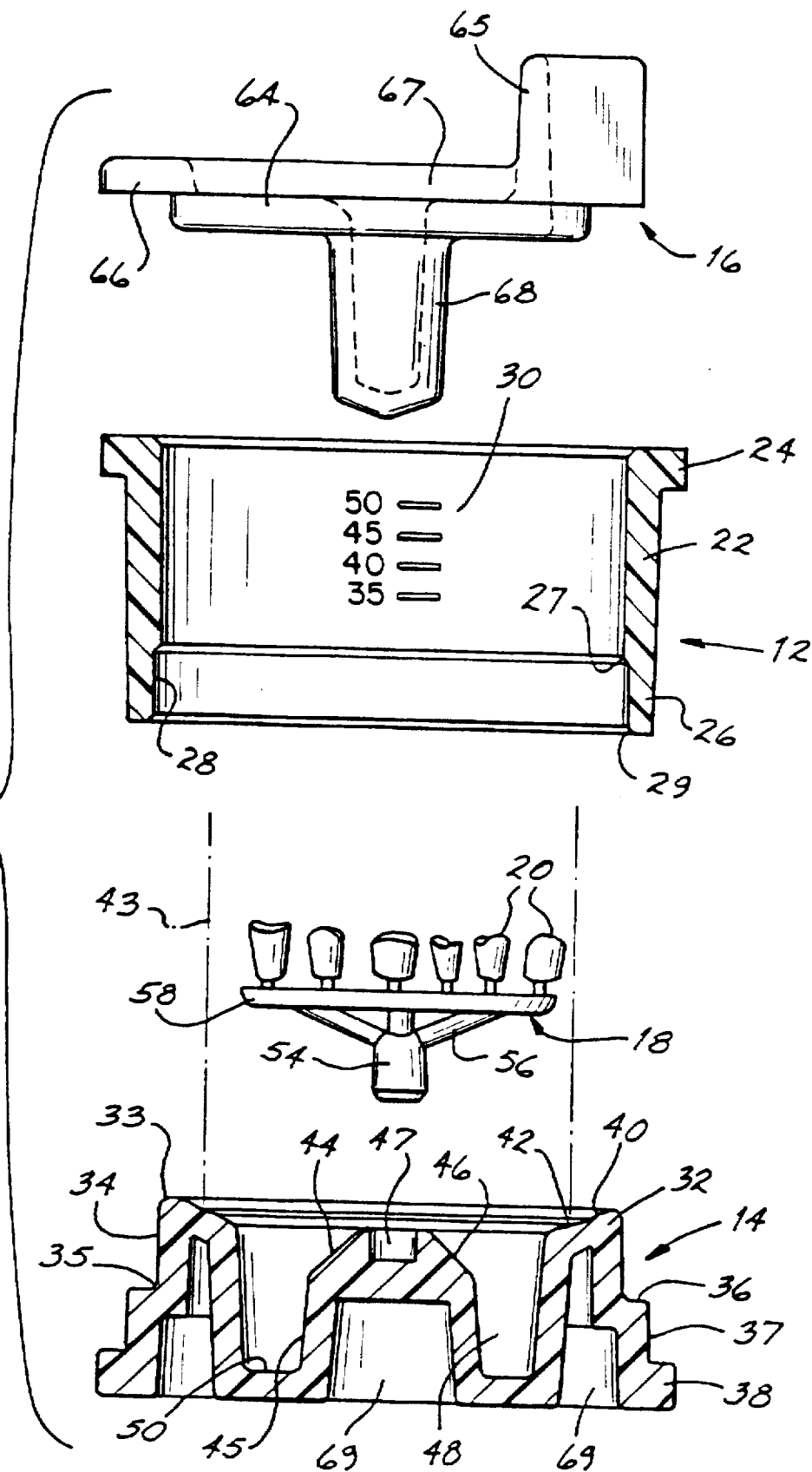
FIG. 1 is an exploded view of the present invention including elastomer base, casing and cover, as well as plastic or wax sprue and wax forms.

Referring to the drawings in particular, the invention embodied in FIG. 1 comprises a mold and sprue combination for use in investment castings which in turn are used for making precision metal castings. The invention comprises a casing 12 having open upper and lower ends, a base 14 which is frictionally engaged to the lower end of the casing, and a cover 16 frictionally engaged with upper end of the casing. The casing, base and cover are all preferably made of the same elastomeric material such as PVC and are advantageously transparent.

A spoked sprue generally designated 18 is attached to base 14 and extends in the volume formed by the vessel comprising the casing, base and cover. A plurality of wax forms 20 are arranged on the upper surface of the sprue. The sprue 18 and forms 20 can be made of the same or different wax or plastic material which is capable of being "burned out" of the investment casting as part of the lost wax casting technique.

Casing 12 has a substantially cylindrical side wall 22 with an outwardly extending stiffening rim 24 extending around its upper open end, and a relatively thin wall cylindrical collar 26 around its lower open end. Collar 26 has an outer surface which is co-extensive with the outer surface of wall 22, and an inner surface 28 bounded at its upper end by an inwardly extending shoulder or bevel 27 and at its lower end by an outwardly extending bevel 29.

A plurality of vertically spaced embossed graduation markings 30 are provided on the inner surface of cylindrical wall 22. Each marking includes a horizontal mark and a numeric value. The term embossed is meant to include both raised markings 30 and indented markings 30. If raised markings are used, they will be transferred in the form of indented markings in the cured and hardened investment casting. If indented markings 30 are used, they will be transformed into raised markings on the outer surface of the investment casting. For the present invention, raised markings 30 on casting 12 are preferred, since indented markings on the outer surface of the brittle investment casting are preferred.

Base 14 includes a thick cylindrical neck 32 having a stepped outer surface which defines a small diameter cylindrical surface 34 bounded at the top and bottom by respective inwardly and outwardly extending bevels 33 and 35. Bevels 27, 29 and inner surface 28 of the collar 26 frictionally engage the bevels 33, 35 and outer surface 34 of base 14 to seal the casing to the base. The lower flat surface of casing 12 engages against a ring shaped platform surface 36 which is formed below bevel 35 in base 14. The outer large diameter surface 37 of base 14 has the same diameter as the outer surface of wall 22. A lower stiffening rim 38 extends radially outwardly at the lower end of base 14 and compliments the upper rim 24 to reinforce the circular shape of the mold in its assembled condition, and help separate the mold parts when held in the hands of a lab technician.

It is noted that the generally axially extending surfaces of the mold, such as the surfaces 28, 34, 37 and inner and outer surfaces of wall 22, are generally cylindrical, but in fact, they have a slight taper of 1 or 2%, as needed to extract the mold parts from equipment for making the mold parts.

Neck 32 includes an upper tapering or conical surface 40. A raised circular sighting bead 42 is provided on surface 40 intermediate the inner and outer surfaces of neck 32. The sighting bead may be closer to the outer surface or closer to the inner surface as desired. The purpose of sighting bead 42 is to provide a visual aide for the laboratory technician in placing the wax forms 20. The lab technician must insure that all wax forms 20 are placed within an imaginary cylindrical surface extending vertically from bead 42 and shown by the phantom line 43. This insures that in the final investment casting, a minimum wall thickness of investment material exists around the wax forms. The sighting bead 42 is used after the sprue 18 has been seated in the base 14 as will be described.

Base 14 also includes a central conical hub 44 which forms a funnel in the end of the investment casting which will communicate with the gates and channels formed by the sprue 18 and forms 20.

Hub 44 includes a tapered base 45 and a conical post receiver 46 having a central generally cylindrical blind hole or bore 47 therein.

A ring shaped groove 48 is defined between hub 44 and neck 32. The combination of the hub 44 and thick neck 32 reduces the circumferential wall thickness of the funnel portion of the investment casting (see investment casting funnel wall 72 in FIG. 10).

A floor surface 50 extends radially between the hub and neck, forming the bottom inside surface of the base.

Figure 3:
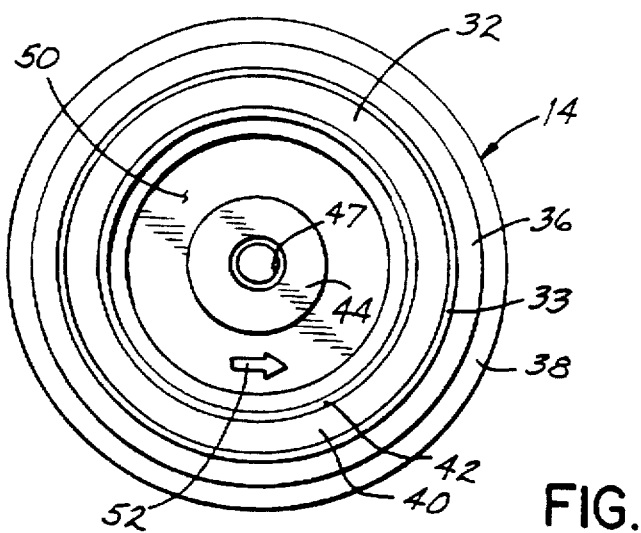
FIG. 3 is a top plan view of the base of the present invention.

As best shown in FIG. 3, an embossed direction marking 52, advantageously in the form of an arrow, is provided at a selected location around the floor surface 50. Here again, the term embossed is used to designate both a raised or an indented marking but the raised marking is preferred to form an indented corresponding marking in the top surface of the funnel wall of the investment casting. This direction marking is valuable to the laboratory technician who has positioned the wax forms 20 while viewing the marking 52 before the investment casting has been formed and who is given an indication of the placement and position of the wax forms in the investment casting after it has hardened, even though the forms are completely invisible within the body of the casting.

Figure 7:
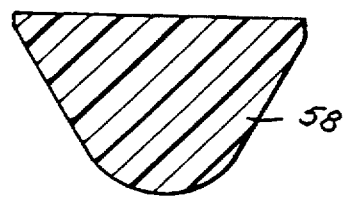
Figure 8:
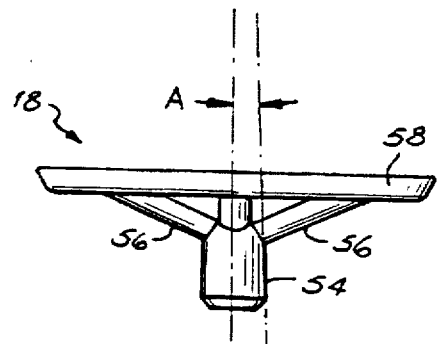
FIG. 8 is a side elevational view of the sprue of the present invention.
Figure 9:
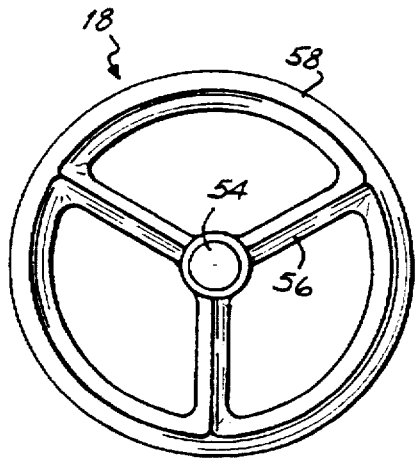
FIG. 9 is a bottom plan view of the sprue of the invention.

As shown in FIGS. 1 and 8, the spoked sprue 18 has a taper post 54 with a beveled lower end at the large diameter of the taper and a smaller end at the top, from which three radially extending spokes 56 extend outwardly and upwardly from the post. The large diameter lower end of post 54 and the direction of its taper helps firmly seal the wax or soft plastic post in the blind bore 47 of the base. A sprue ring 58 is connected to the outer ends of the spokes 56. Referring now to FIGS. 5-9, FIG. 8 shows an angle A between the outer surface of tapered post 54 and the axis of sprue 18

Figure 5:
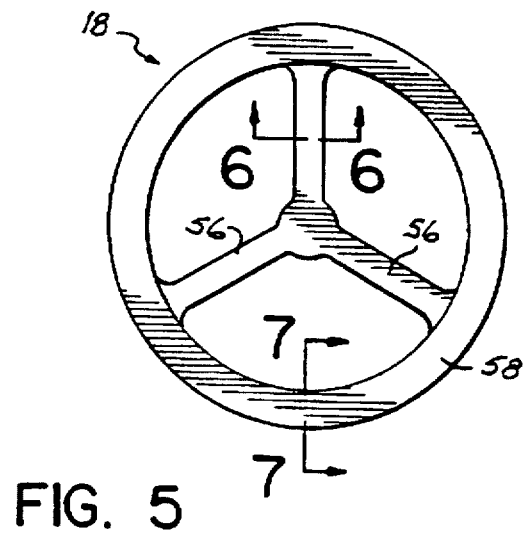
FIG. 5 is a top plan view of the spoked sprue with ring of the present invention.

As shown at FIG. 5, the 3 spokes 56 are spaced at equal distances around the center of the sprue. Although three spokes have been found to be optimum for creating the gate channels for the passage of molten metal to the voids created by the wax forms 20, the invention is intended to include two or more spokes spaced by equal amounts around the center of the sprue and more advantageously, three or more spokes.

Figure 6:
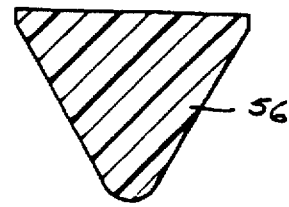
FIGS. 6 and 7 are sectional views of the spoke and ring respectively, taken along lines 6—6 and 7—7 of FIGS. 6 and 7 respectively.

Another important advantage of the invention is the fact that each of the spokes 56 and the ring 58 are substantially triangular in cross-section as shown in FIGS. 6 and 7. Although the bottom apex of the spokes and ring is advantageously rounded, the top surface is flat. This creates a gate system in the lost wax process which is likewise triangular in cross section, which has been found to increase the filling rate of the system with molten metal, and also saves approximately 40% of the metal in the ultimate precision casting which is otherwise wasted in the sprue systems having round cross sections. Another advantage to the flat topped configuration of the ring 58 is that it facilitates arrangement and mounting of the wax forms 20 on the flat surface. The lab technician need not have the difficulty of balancing wax forms on a curved upper surface, but rather is provided with a flat convenient surface to work on. This is further enhanced by the sighting bead 42.

Figure 10:
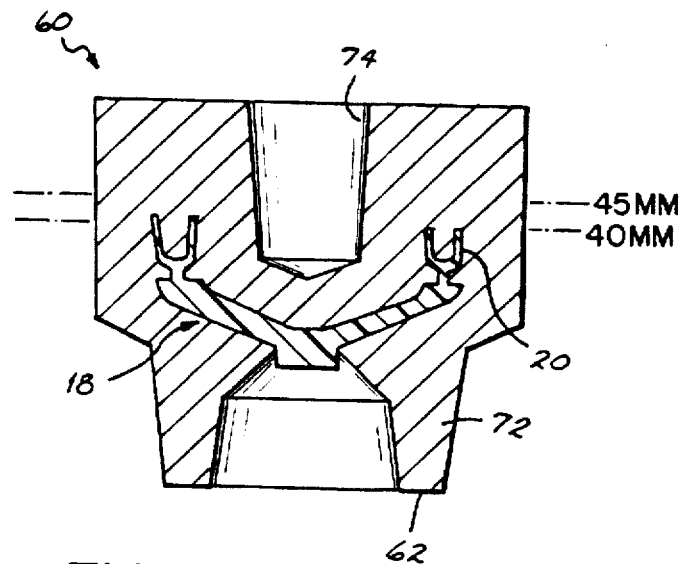
FIG. 10 is a cross-sectional view of the investment casting with embedded wax sprue and forms, before they are burned out of the investment, in preparation for shooting molten metal for making a precision casting of the same shape.

Returning to FIG. 1, with the sprue 18 engaged to the base 14 (not shown) and the casing 12 and cover 16 engaged to each other to form the closed vessel (not shown), the graduation markings 50 are used to show the maximum vertical height of the highest wax form 20 in the vessel. This measurement is noted by the laboratory technician. In the process of pouring the liquid investment solution into the mold vessel, the lab technician fills the vessel to a level of about 10 mm or greater above the highest wax form. Keeping in mind that the vertical graduations remain as indentations on the outer surface of the investment casting. Referring to FIG. 10, after the casting shown at 60 in FIG. 10 has cured and hardened and is removed from the mol da the laboratory technician, knowing the internal position of the sprue 18 (which would form a precision casting in the investment) will select a location approximately 5 millimeters above the highest wax form (which was previously noted). For example, if the highest wax form is at 40 mm, this position is known and shown by the lower dashed lines in FIG. 10. A level 5 mm higher (that is, at the 45 mm position) is selected and then can be used to grind away the top portion of the investment casting. This grinding operation in no way endangers the precision casting as a margin of 5 mm is maintained. At the same time, excess weight and unneeded investment material is removed. The direction marking 62 which was left by the embossed direction marking 52 is also available to help the laboratory technician orient the investment casting in an appropriate manner since the technician already knows the position and orientation of the casting within the casting 60, from marking 62.

Figure 2:
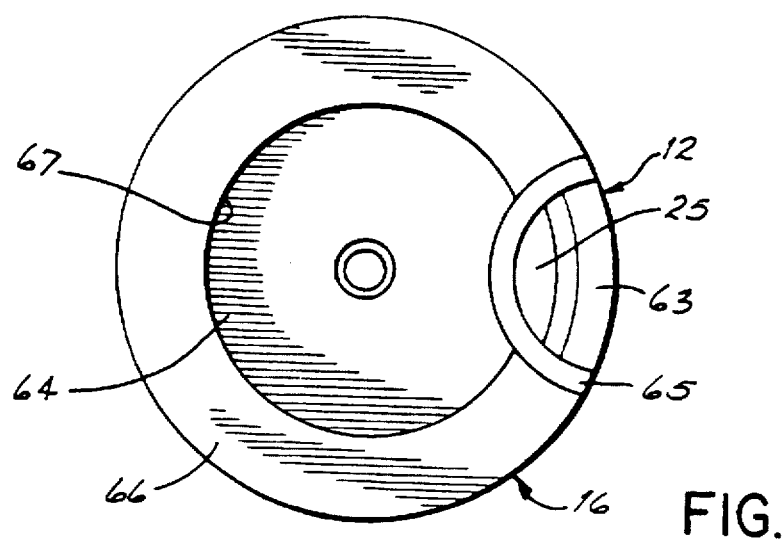
FIG. 2 is a top plan view of the mold of the present invention.

Referring now to FIGS. 1 and 2, cover 16 comprises a disk shaped body 64 having an outwardly extending cover rim 66. Body 64 has an outer diameter that matches the inner diameter of wall 22 and rim 66 fits over the top of stiffening rim 24 of body 22. A curved lip 65 extends vertically from the body and rim and forms a curved recess 63 best shown in FIG. 2. The recess 63 is deep enough so that it exposes a small area of the open top of the body 22, at a hole 25.

In use, the lip 65 and hole 25 are used to facilitate pouring of liquid investment into the mold in a manner disclosed in U.S. Pat. No. 5,469,908.

As noted above, the graduation markings 30 can be used during the filling operation, and with the mold held in an upright position, to provide only as much investment into the vessel as is required to establish a good margin of material above the highest wax form 20.

In order to avoid waste of investment material and even more importantly, in order to establish a substantially uniform thickness of investment material on both sides of the ring shaped pattern of wax forms 20, a tapered plug 68 depends from the center of the lower surface of cover body 64.

As shown in FIG. 10, this creates and upper blind funnel 74. An examination of FIG. 10 will show that there is substantially equal thickness of investment materials on both sides of the wax forms 20. This avoids distortion that would be caused while the investment cures and expands. Curing of the investment is known to involve expansion of the investment material that would cause undesirable constriction and deformation of the form. The use of plug 68 as an integral part of cover 16 automatically centers the plug in the ring shaped configuration and thus simplified the use of the invention over U.S. Pat. No. 4,962,909. U.S. Pat. No. 4,962,909 also provides a blind funnel at the top of the casting but does so in a different manner which requires careful alignment and adjustment for a successful casting operations As shown in FIG. 1, voids 69 are provided inside the hub and neck of base 14 to reduce the amount of material needed to form the base 14. While this results in a hollow neck and hub arrangement, this does not adversely affect the invention in any way. In likewise fashion, a central recess 67 is formed at the top of cover body 64, which recess extends into the center of plug 68. This produces a hollow plug and a lighter weight cover, again without reducing the effectiveness of the present invention.

Figure 4:
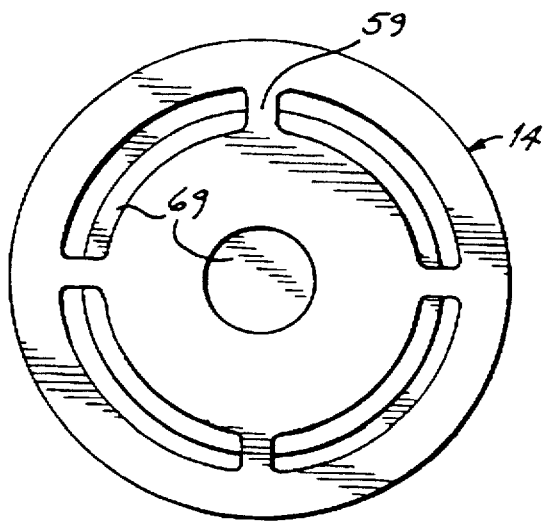
FIG. 4 is a bottom plan view of the base of the present invention.

As shown in FIG. 4, radial ribs 59 are provided to span the void 69 in the neck to stiffen the neck. Although four ribs 59 are shown in FIG. 4, a larger or smaller number of ribs may be used depending on the size of the mold.

According to the present invention, in particular by using the thick walled neck in the base and the blind funnel in the cover, an investment casting which would normally use 300 grams of investment solution only needs 180 grams according to the present invention. A larger investment which would normally use 500 grams only requires 220 grams. This represents savings of $2-$3.00 per investment casting and also reduces distortion in the precision casting. By using triangular spokes and ring in the sprue 18, approximately 40% of the metal in the gate system is saved.

While a specific embodiment of the invention has been shown and described in detail to illustrate the application of the principles of the invention, it will be understood that the invention may be embodied otherwise without departing from such principles.

What is claimed is:

1. A sprue former for a dental investment casting mold, the sprue former comprising:

a post to form a sprue fill port in investment material;

one or more elongated sections connected between the post and one or more pattern support positions to form a sprue in the investment material that will channel a flow of dental molding liquid from the fill port to the pattern support positions;

the elongated sections having a cross-section having a downwardly facing surface with a downwardly extending apex thereon and an upwardly facing surface that is flat relative to the downwardly facing surface.

2. The sprue former of claim 1 wherein:

the elongated sections of the sprue former include a plurality of spokes having inner and outer ends and spaced equally around the post, the inner ends being connected to the hub, the former also having a closed ring connected to the outer ends of each of the spokes and having the support positions located thereon.

3. The sprue former of claim 2 wherein:

the spokes and ring have generally triangular cross-sections.

4. The sprue former of claim 2 wherein:

the spokes and ring have generally flat upper surfaces, and sides converging to an approximate corner at the bottom.

5. The sprue former of claim 2 wherein:

the spokes and ring have generally flat upper surfaces, and sides converging to an approximate corner at the bottom.

6. A sprue former for a dental investment casting mold, the sprue former comprising:

a post to form a sprue fill port in investment material;

one or more elongated sections connected between the post and one or more pattern support positions to form a sprue in the investment material that will channel a flow of dental molding liquid from the fill port to the pattern support positions the elongated sections having a triangular cross-section having a downwardly facing apex and a generally flat upwardly facing surface.

7. The sprue former of claim 6 wherein:

the elongated sections of the sprue former include a plurality of spokes having inner and outer ends and spaced equally around the post, the inner ends being connected to the hub, the former also having a closed ring connected to the outer ends of each of the spokes and having the support positions located thereon.

* * * * *